(12) United States Patent
Lupton et al.

(10) Patent No.: US 12,714,297 B2
(45) Date of Patent: Aug. 25, 2026

(54) ENDOSCOPE WITH PIVOTING LIGHTING

(71) Applicant: COOK MEDICAL TECHNOLOGIES LLC, Bloomington, IN (US)

(72) Inventors: Jonathan K. Lupton, Thomasville, NC (US); Liam Breen, Ballina (IE); Vincent McHugo, Birdhill (IE); John C. Sigmon, Jr., Winston-Salem, NC (US); Shaun D. Gittard, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 469 days.

(21) Appl. No.: 18/170,668

(22) Filed: Feb. 17, 2023

(65) Prior Publication Data

US 2023/0263379 A1 Aug. 24, 2023

Related U.S. Application Data

(60) Provisional application No. 63/313,061, filed on Feb. 23, 2022.

(51) Int. Cl.

| | |
|---|---|
| ***A61B 1/06*** | (2006.01) |
| ***A61B 1/00*** | (2006.01) |
| ***A61B 1/012*** | (2006.01) |

(52) U.S. Cl.

CPC ........ *A61B 1/0627* (2022.02); *A61B 1/00096* (2013.01); *A61B 1/00114* (2013.01); *A61B 1/012* (2013.01); *A61B 1/0676* (2013.01)

(58) Field of Classification Search

CPC ............ A61B 1/00027; A61B 1/00029; A61B 1/00183; A61B 1/0627

See application file for complete search history.

(56) References Cited

U.S. PATENT DOCUMENTS

| | | | |
|---|---|---|---|
| 3,557,780 | A | 1/1971 | Sato |
| 3,896,793 | A | 7/1975 | Mitsui et al. |
| 4,763,662 | A | 8/1988 | Yokoi |
| 5,005,558 | A | 4/1991 | Aomori |
| 5,143,475 | A | 9/1992 | Chikama |

(Continued)

FOREIGN PATENT DOCUMENTS

| | | | |
|---|---|---|---|
| CN | 105078398 | A | 11/2015 |
| EP | 2596741 | A1 | 5/2013 |

(Continued)

OTHER PUBLICATIONS

Written Opinion in International Patent Application No. PCT/US2023/062795 dated Sep. 12, 2023, 4 pages.

(Continued)

*Primary Examiner* — Alexandra L Newton

(74) *Attorney, Agent, or Firm* — Vivacqua Crane, PLLC

(57) ABSTRACT

A scope system is provided including an elongate tube with a distal portion and a lumen extending therethrough, the distal portion comprising a distal end section comprising a pivot arm, the scope system further comprising a plurality of lights distributed on and connected to the distal end section and the pivot arm. The plurality of lights is configured to be connected by an electrical wire and/or a conductor to a power source.

13 Claims, 6 Drawing Sheets

(56) References Cited

U.S. PATENT DOCUMENTS

| | | | | |
|---|---|---|---|---|
| 5,749,828 | A | 5/1998 | Solomon et al. | |
| 5,873,817 | A | 2/1999 | Kokish et al. | |
| 6,071,279 | A | 6/2000 | Whayne et al. | |
| 6,817,974 | B2 | 11/2004 | Cooper et al. | |
| 8,771,171 | B2 | 7/2014 | Onuki et al. | |
| 9,408,529 | B2 | 8/2016 | Smith et al. | |
| 9,565,994 | B2 | 2/2017 | Kappel et al. | |
| 9,986,996 | B2 | 6/2018 | Hiernaux et al. | |
| 10,029,073 | B2 | 7/2018 | Kabe et al. | |
| 10,076,236 | B2 | 9/2018 | Ikeda et al. | |
| 10,321,804 | B2 | 6/2019 | Jacobsen et al. | |
| 10,363,398 | B2 | 7/2019 | Gerrans et al. | |
| 11,503,984 | B2 | 11/2022 | Surti et al. | |
| 2004/0138529 | A1 | 7/2004 | Wiltshire et al. | |
| 2004/0249367 | A1 | 12/2004 | Saadat et al. | |
| 2005/0234297 | A1 | 10/2005 | Devierre et al. | |
| 2006/0178560 | A1 | 8/2006 | Saadat et al. | |
| 2006/0189845 | A1 | 8/2006 | Maahs et al. | |
| 2008/0097293 | A1 | 4/2008 | Chin | |
| 2008/0287961 | A1 | 11/2008 | Miyamoto et al. | |
| 2008/0300462 | A1 | 12/2008 | Intoccia et al. | |
| 2009/0171159 | A1 | 7/2009 | Jorgensen | |
| 2010/0036168 | A1 | 2/2010 | Tacchino et al. | |
| 2012/0041264 | A1 | 2/2012 | Blase | |
| 2012/0170970 | A1 | 7/2012 | Kitagawa et al. | |
| 2012/0184820 | A1 | 7/2012 | Dahmen et al. | |
| 2012/0238805 | A1 | 9/2012 | Iwasaka | |
| 2013/0184528 | A1 | 7/2013 | Onuki et al. | |
| 2013/0231534 | A1 | 9/2013 | Piskun et al. | |
| 2014/0142393 | A1 | 5/2014 | Piskun et al. | |
| 2015/0032117 | A1 | 1/2015 | Kim et al. | |
| 2015/0101442 | A1 | 4/2015 | Romo | |
| 2016/0235400 | A1 | 8/2016 | Hiernaux et al. | |
| 2016/0288337 | A1 | 10/2016 | Zubiate et al. | |
| 2017/0095645 | A1 | 4/2017 | Toth | |
| 2017/0251908 | A1* | 9/2017 | Surti | A61B 1/0684 |
| 2017/0354318 | A1 | 12/2017 | Rogers et al. | |
| 2018/0168432 | A1 | 6/2018 | Banik et al. | |
| 2018/0360435 | A1 | 12/2018 | Romo | |
| 2019/0104932 | A1 | 4/2019 | Ostrovsky et al. | |
| 2019/0142413 | A1 | 5/2019 | Fairneny | |
| 2022/0175219 | A1* | 6/2022 | Schwarz | A61B 1/00103 |
| 2024/0423461 | A1* | 12/2024 | O'Callaghan | A61B 1/00126 |

FOREIGN PATENT DOCUMENTS

| | | | |
|---|---|---|---|
| GB | 2478988 | | 9/2011 |
| JP | S61-280849 | A | 12/1986 |
| JP | S62-74348 | A | 4/1987 |
| JP | S62-292135 | A | 12/1987 |
| JP | S63-155116 | A | 6/1988 |
| JP | H01-138522 | A | 5/1989 |
| JP | H10-295635 | A | 11/1998 |
| JP | 2003-204926 | A | 7/2003 |
| JP | 2005-152452 | A | 6/2005 |
| JP | 2007-532262 | A | 11/2007 |
| JP | 2008-536552 | A | 9/2008 |
| JP | 2009-018044 | A | 1/2009 |
| JP | 2009-529390 | A | 8/2009 |
| JP | 2010-063772 | A | 3/2010 |
| JP | 2010-284503 | A | 12/2010 |
| JP | 2011-062362 | A | 3/2011 |
| JP | 2011-072413 | A | 4/2011 |
| JP | 2013-066638 | A | 4/2013 |
| JP | 2014-102390 | A | 6/2014 |
| JP | 2015-512661 | A | 4/2015 |
| JP | 2016-513500 | A | 5/2016 |
| JP | 2018531058 | A | 10/2018 |
| JP | 2019508145 | A | 3/2019 |
| KR | 10-2012-0111603 | | 10/2012 |
| WO | WO 2007/063904 | A1 | 6/2007 |
| WO | WO 2012/111761 | A1 | 8/2012 |
| WO | 2017040692 | A1 | 3/2017 |
| WO | 2017151559 | A1 | 9/2017 |

OTHER PUBLICATIONS

International Search Report and Written Opinion in International Patent Application No. PCT/US2023/062795 dated Jun. 9, 2023, 13 pages.

International Preliminary Report on Patentability in PCT Application No. PCT/US2023/062795, dated May 7, 2024 (13 pages).

Japan Patent Office. Notice of Reasons for Refusal for JP Application No. 2024-553747 and English translation, mailed Aug. 12, 2025, pp. 1-7.

* cited by examiner

ENDOSCOPE WITH PIVOTING LIGHTING

CROSS-REFERENCE TO RELATED APPLICATIONS

The present application claims the benefit of U.S. Provisional Application No. 63/313,061, filed Feb. 23, 2022, which is incorporated by reference herein in its entirety for all purposes.

FIELD

The present disclosure relates to medical devices. More particularly, the disclosure addresses the need for lighting in both forward and side-viewing configurations of endoscope systems.

BACKGROUND

The statements in this section merely provide background information related to the present disclosure and may not constitute prior art.

Internal body cavities and body lumens may become blocked, or the walls surrounding them may develop growths. In some cases, removal of these blockages or growths, or other treatment thereof, may be necessary. Endoscopic or other minimally invasive techniques may be used to treat these situations.

One type of treatment includes the use of catheters or other endoscopic devices that are inserted into the body lumen or cavity and toward the area where treatment is desired. Insertion of the endoscope to the target area can allow for visualization of the target area and a determination of the desired procedure and the specific location of the area to be treated.

In general, endoscopes have been designed to be operated with the same fundamental mechanisms, and have not had transformational improvements. Endoscopes generally include a camera and a set of wheels that an operator, such as a physician, operates with a first hand (in some cases, the left hand) to control scope deflection, while the second (generally, right) hand switches between the insertion tube of the endoscope and the accessory channel in order to control scope and device advancement, respectively, through the anatomy of a patient.

When performing an Endoscopic Retrograde Cholangiopancreatography ("ERCP") procedure with a duodenoscope and cholangioscope, navigating to the duodenum and cannulating the papilla require varying degrees of lighting for the endoscope camera systems for large and small cavities, and/or distant and close anatomical features. Particularly, the large cavity of the stomach requires brighter lighting than in the smaller cavity of the duodenum or the even smaller cavity of the biliary duct. In addition to brightness, the direction and placement of the lighting elements on an endoscope play a critical role in the illumination of a patient's anatomy and the overall image quality of the endoscope during a procedure. Maintaining lighting illumination with the camera element provides the best performance, while limiting the required quantity, size, and brightness of lighting components.

The placement of lighting elements also plays a critical role in reducing shadowing from device mechanical features, catheter or accessory extension, or a patient's anatomical features. When lighting elements are placed near the endoscope edges, or around outer diameter bounds, then anatomical features may block illumination or cause excessive shadowing of relevant anatomy distal to the endoscope view. Cholangioscope or accessory extension from a duodenoscope must be considered when placing lighting elements in order to limit extension devices from causing illumination shadowing behind the devices relative to the camera view.

Specialized endoscopes are becoming more common in the field of endoscopy. The camera and working channels of specialized endoscopes may be oriented through the full range of forward-viewing to side viewing configurations. Lighting elements have generally only been placed on the non-pivoting distal end section of a specialized endoscope, with no placement of lighting elements on any components at the distal end that can pivot or rotate that would allow angulation of light relative to the axis of the elongate tube of the endoscope. Lighting elements placed only on the distal end section may limit image illumination, because alignment between the camera and lighting elements will not be maintained.

SUMMARY

In an example, the present disclosure provides a scope system. The scope system includes an elongate tube including a lumen extending therethrough, the elongate tube further including a distal portion including a distal end section, the distal end section including a pivot arm, the distal end section defining a forward direction parallel to a longitudinal direction of the distal end section. The scope system further includes at least one accessory channel comprising a tubular structure, the tubular structure including an accessory lumen extending therethrough, the at least one accessory channel movably disposed at least partially within the lumen of the elongate tube, the at least one accessory channel including a distal section, the at least one accessory channel being movable between a forward-viewing configuration and a side-viewing configuration. A distal end of the at least one accessory channel is attached to the pivot arm. The scope system further includes a plurality of lights located on and connected to the distal end section. In the forward-viewing configuration, the distal section of the at least one accessory channel substantially faces in the forward direction. In the side-viewing configuration, the distal section of the at least one accessory channel faces a direction that is angled relative to the forward direction. During movement of the at least one accessory channel between the forward-viewing configuration and the side-viewing configuration, the at least one accessory channel and the pivot arm rotate about a pivot point, the pivot point fixed relative to the distal end section of the elongate tube. One or more of the plurality of lights are distributed on and connected to the pivot arm. The pivot arm may be connected to the distal end section by a pivot point support member defining the pivot point, and the pivot point support member may include an electrical wire configured to connect the plurality of lights to a power source. The pivot arm may be connected to the distal end section by a pivot point support member defining the pivot point, and the pivot point support member may include an internal cavity including an electrical wire configured to connect the one or more of the plurality of lights distributed on and connected to the pivot arm to a power source. The pivot arm may include at least one conductor configured to contact a second conductor of the distal end section throughout movement of the at least one accessory channel between the forward-viewing configuration and the side-viewing configuration. The at least one accessory channel may include a fiber optic lighting cable in a dedicated lumen in the at least one accessory channel, in overmolding on the at least one accessory channel, and/or within or along a wall of the at least one accessory channel. The pivot arm and/or the distal end section may each be independently fully transparent, partially transparent, or non-transparent. The scope system may further include a power source connected to the plurality of lights. The at least one accessory channel may be configured to secure an electrical wire connecting the plurality of lights to a power source, and to permit free movement of the electrical wire during movement of the at least one accessory channel. The distal portion may include a plurality of individual ribs, at least one of the plurality of individual ribs including a substantially U-shaped cross-section including two sides and an opening, and the plurality of individual ribs may be configured to secure an electrical wire connecting the plurality of lights to a power source, and to permit free movement of the electrical wire during movement of the at least one accessory channel and/or bending of the distal portion.

In another example, the present disclosure provides a scope system. The scope system includes an elongate tube including a distal portion including a distal end section, the distal end section including a pivot arm, the distal end section defining a forward direction parallel to a longitudinal direction of the distal end section. The scope system further includes at least one accessory channel including a tubular structure, the tubular structure including an accessory lumen extending therethrough, the at least one accessory channel movably disposed at least partially within the lumen of the elongate tube, the at least one accessory channel including a distal section, the at least one accessory channel being movable between a forward-viewing configuration and a side-viewing configuration, a distal end of the at least one accessory channel connected to the pivot arm. The scope system further includes a plurality of lights located on and connected to the distal end section. The scope system further includes first and second deflection cables connected to the distal portion of the elongate tube and extending proximally along the elongate tube. In the forward-viewing configuration, the distal section of the at least one accessory channel substantially faces in the forward direction. In the side-viewing configuration, the distal section of the at least one accessory channel faces a direction that is angled relative to the forward direction. The distal end section includes a pivot arm, wherein during movement of the at least one accessory channel between the forward-viewing configuration and the side-viewing configuration, the at least one accessory channel and the pivot arm rotate about a pivot point, the pivot point fixed relative to the distal end section of the elongate tube. One or more of the plurality of lights are distributed on and connected to the pivot arm. Proximal movement of the first deflection cable bends the distal portion of the elongate tube in a first direction, and proximal movement of the second deflection cable bends the distal portion of the elongate tube in a second direction, the second direction opposite the first direction. The pivot arm may be connected to the distal end section by a pivot point support member defining the pivot point, and the pivot point support member may include an electrical wire configured to connect the plurality of lights to a power source. The pivot arm may be connected to the distal end section by a pivot point support member defining the pivot point, and the pivot point support member may include an internal cavity including an electrical wire configured to connect the one or more of the plurality of lights distributed on and connected to the pivot arm to a power source. The pivot arm may include conductive features configured to contact conductive features on the distal end section throughout movement of the at least one accessory channel between the forward-viewing configuration and the side-viewing configuration. The at least one accessory channel may include a fiber optic lighting cable in a dedicated lumen in the at least one accessory channel, in overmolding on the at least one accessory channel, and/or within or along a wall of the at least one accessory channel. The pivot arm and/or the distal end section may each be independently fully transparent, partially transparent, or non-transparent. The scope system may further include a power source connected to the plurality of lights. The at least one accessory channel may be configured to secure an electrical wire connecting the plurality of lights to a power source, and to permit free movement of the electrical wire during movement of the at least one accessory channel. The distal portion may include a plurality of individual ribs, at least one of the plurality of ribs including a substantially U-shaped cross-section including two sides and an opening, and the plurality of individual ribs may be configured to secure an electrical wire connecting the plurality of lights to a power source, and to permit free movement of the electrical wire during movement of the at least one accessory channel and/or bending of the distal portion. The first deflection cable and/or the second deflection cable may be configured to secure an electrical wire connecting the plurality of lights to a power source, and to permit free movement of the electrical wire during movement of the at least one accessory channel and/or bending of the distal portion.

In yet another example, the present disclosure provides a scope system. The scope system includes an elongate tube including a lumen extending therethrough and a distal end section. The scope system further includes an accessory channel movably disposed at least partially within the lumen of the elongate tube. A distal section of the accessory channel is rotatably moveable about a pivot point between a forward-facing direction and an angled direction, the pivot point being fixed relative to the distal end section of the elongate tube. The light is fixed to the distal section of the accessory channel such that when the distal section of the accessory channel rotates between the forward-facing direction and the angled direction, the light also rotates relative to the distal end section of the accessory channel.

Further areas of applicability will become apparent from the description provided herein. It should be understood that the description and specific examples are intended for purposes of illustration only and are not intended to limit the scope of the present disclosure.

DRAWINGS

In order that the present disclosure may be well understood, there will now be described various forms thereof, given by way of example, reference being made to the accompanying drawings. The components in the figures are not necessarily to scale. Moreover, in the figures, like-referenced numerals designate corresponding parts through the different views.

Figure 1:
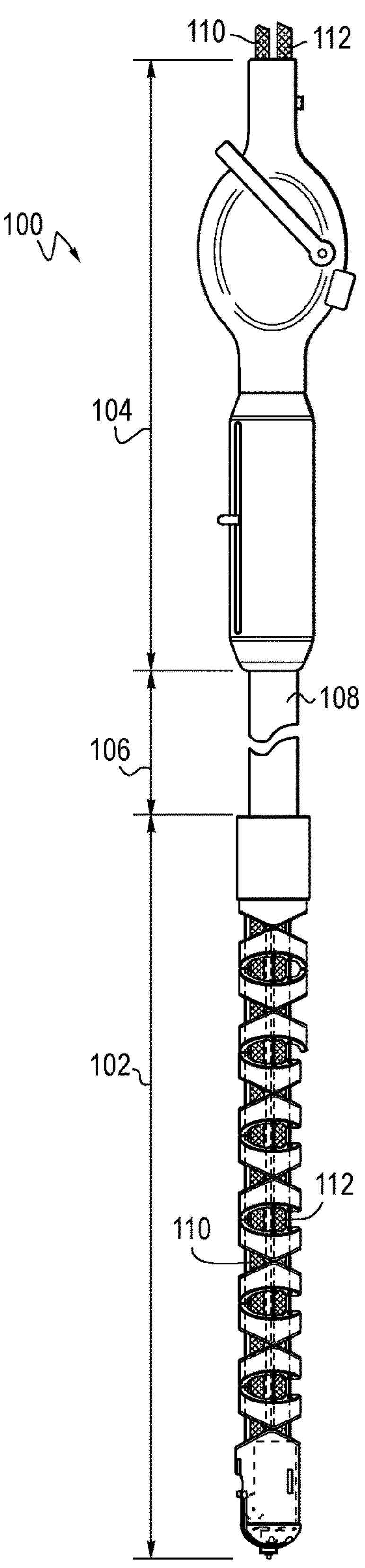
FIG. 1 illustrates a side view of an example of a steerable endoscopic system, according to the principles of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In adding reference denotations to elements of each drawing, although the same elements are displayed on a different drawing, it should be noted that the same elements have the same denotations. In addition, in describing one aspect of the present disclosure, if it is determined that a detailed description of related well-known configurations or functions blurs the gist of one aspect of the present disclosure, it will be omitted.

In the following discussion, the terms "proximal" and "distal" will be used to describe the opposing axial ends of the device, as well as the axial ends of various component features. The term "proximal" is used in its conventional sense to refer to the end of the device (or component) that is closest to the medical professional during use of the assembly. The term "distal" is used in its conventional sense to refer to the end of the device (or component) that is initially inserted into the patient, or that is closest to the patient during use. The term "longitudinal" will be used to refer to an axis that aligns with the proximal-distal axis of the device (or component). The terms "radially" and "radial" will be used to refer to elements, surfaces, or assemblies relative to one another that may extend perpendicularly from a longitudinal axis. The terms "circumference," "circumferentially," and "circumferential" will be used to refer to elements, surfaces, or assemblies relative to one another encircling a longitudinal axis at a radius.

The uses of the terms "a" and "an" and "the" and similar referents in the context of describing the present disclosure (especially in the context of the following claims) are to be construed to cover both the singular and the plural, unless otherwise indicated herein or clearly contradicted by context. The use of the term "plurality of" is defined by the Applicant in the broadest sense, superseding any other implied definitions or limitations hereinbefore or hereinafter unless expressly asserted by the Applicant to the contrary, to mean a quantity of more than one. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein the terms "comprise(s)," "include(s)," "having," "has," "can," "contain(s)," and variants thereof, are intended to be open-ended transitional phrases, terms, or words that do not preclude the possibility of additional acts or structures. The present description also contemplates other examples "comprising," "consisting of," and "consisting essentially of," the examples or elements presented herein, whether explicitly set forth or not.

In describing elements of the present disclosure, the terms $1^{st}$, $2^{nd}$ first, second, A, B, (a), (b), and the like may be used herein. These terms are only used to distinguish one element from another element, but do not limit the corresponding elements irrespective of the nature or order of the corresponding elements.

Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

As used herein, the term "about," when used in the context of a numerical value or range set forth means a variation of ±15%, or less, of the numerical value. For example, a value differing by ±15%, ±14%, ±10%, or ±5%, among others, would satisfy the definition of "about," unless more narrowly defined in particular instances.

Referring to FIG. 1, an example of an endoscope system 100 is illustrated. Endoscope system 100 may be generally shaped as an elongate tube including distal portion 102, central portion 106, and a proximal, or handle, portion 104. Central portion 106 may be a flexible, elongate tube with at least one lumen 108 running throughout the length of central portion 106. Central portion 106 may connect distal portion 102 and handle portion 104 together. Lumen 108 of central portion 106 may extend through distal portion 102 and handle portion 104 of endoscope system 100 as well. Central portion 106 may be made of a braided material such as pebax with a polytetrafluoroethylene liner to provide sufficient torqueability and pushability. Other potential materials for central portion 106 include but are not limited to polyethylene, polypropylene, and nylon. Endoscope system 100 may further include two accessory channels 110, 112 each with a lumen running therethrough. First accessory channel 110 and second accessory channel 112 may be designed as individual elongated tubes that may be movable within lumen 108 of endoscope system 100, thus allowing longitudinal movement of first accessory channel 110 and second accessory channel 112 with respect to central portion 106. While the example of endoscope system 100 includes two accessory channels, first accessory channel 110 and second accessory channel 112, one or even three or more accessory channels may be used. For example, a single, larger accessory channel may be used to accommodate larger endoscopic tools. Further, in lieu of individual first accessory channel 110 and second accessory channel 112, a single elongate tube may be used with two or more lumens running through it. First accessory channel 110 and second accessory channel 112 may range in diameter anywhere from 1 to 10 millimeters. In certain examples, first accessory channel 110 may be 4.2 millimeters in diameter while second accessory channel 112 may be 3.7 millimeters in diameter. First accessory channel 110 and second accessory channel 112 may extend proximally from or past handle portion 104, through lumen 108 and into distal portion 102. Various tools, devices, and cameras may be inserted into and removed from first accessory channel 110 and second accessory channel 112.

Figure 2:
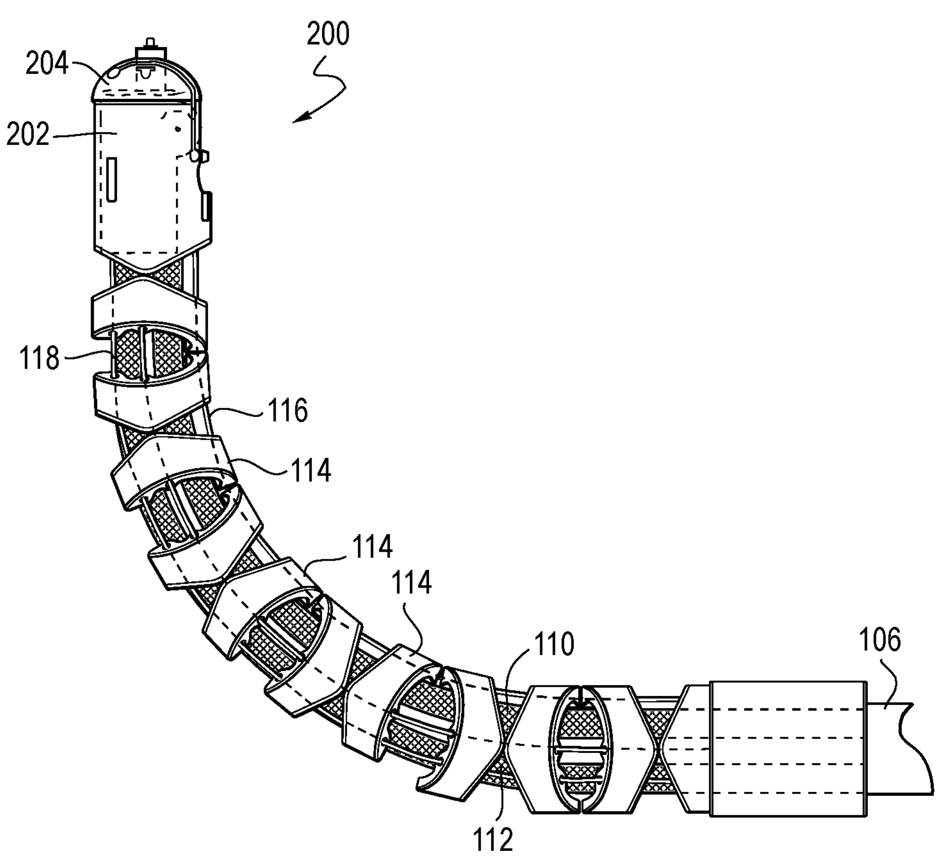
FIG. 2 illustrates a side view of an example of a distal portion of a steerable endoscopic system in a bent configuration, according to the principles of the present disclosure.

Referring to FIG. 2, a side view of an example of a distal portion 200 of a steerable endoscopic system in a bent configuration is illustrated. Distal portion 200 may have a flexible, rib-like construction with multiple individual ribs 114 connected together to create an elongate tube with a lumen. Ribs 114 may be made of a variety of materials, such as polycarbonate, nylon, polyethylene, polypropylene, and polyoxymethylene. First accessory channel 110 and second accessory channel 112 may extend through ribs 114 to distal end section 202 of distal portion 200.

Figure 3:
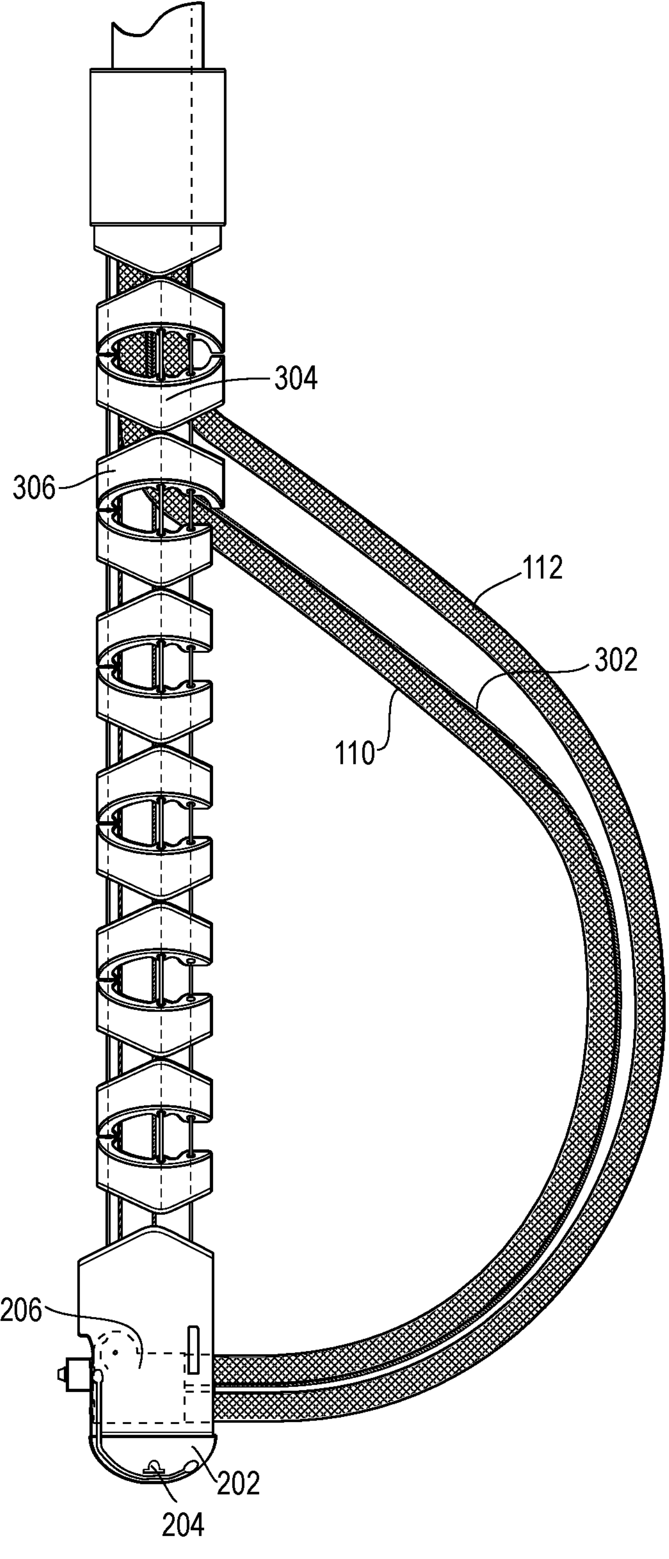
FIG. 3 illustrates a side view of another example of a distal portion of a steerable endoscopic system in a side-viewing configuration, according to the principles of the present disclosure.

Distal end section 202 may define a forward direction parallel to a longitudinal direction of distal end section 202. Distal end section 202 may include a pivot arm 206. Pivot arm 206 may be connected to distal end section 202 by pivot point support member 208. Pivot point support member 208 may create a pivot point, around which pivot arm 206 may rotate with respect to distal end section 202 to the position illustrated in FIG. 3. Pivot arm 206 may be moved between a forward-viewing configuration as illustrated in FIGS. 1 and 2, and a side-viewing configuration as illustrated in FIG. 3. In the forward-viewing configuration, the distal section of first accessory channel 110 and second accessory channel 112 substantially face in the forward direction. In the side-viewing configuration, the distal section of first accessory channel 110 and second accessory channel 112 substantially face a direction that is angled relative to the forward direction. A light-emitting diode ("LED") light 204 or a plurality of LED lights 204 is located on distal end section 202 to assist in navigation through a patient's GI tract. Alternatively, LED light 204 or plurality of LED lights 204 may be located at other locations on distal end section 202 such as pivot arm 206. LED light 204 or plurality of LED lights 204 may be distributed on, located on, or connected to pivot arm 206 and/or distal end section 202.

As illustrated in FIG. 3, the distal ends of first accessory channel 110 and second accessory channel 112 may be secured to pivot arm 206. Therefore, first accessory channel 110 and second accessory channel 112 may rotate with pivot arm 206 when moving pivot arm 206 between side-viewing and forward-viewing configurations. FIGS. 1 and 2 illustrate first accessory channel 110 and second accessory channel 112 in the forward-viewing configuration, while FIG. 3 illustrates first accessory channel 110 and second accessory channel 112 in the side-viewing configuration. As illustrated in FIG. 3, when in the side-viewing configuration and due to rotation of pivot arm 206, distal portions of first accessory channel 110 and second accessory channel 112 are bent outside of the confines of ribs 114 and then curve back towards and into pivot arm 206. Thus, in the forward-viewing configuration, the angle of curvature or bending radius of distal end section 202 is the same as the angle of curvature of first accessory channel 110 and second accessory channel 112 such that first accessory channel 110, second accessory channel 112, and distal end section 202 of endoscope system 100 are substantially parallel; but in the side-viewing configuration, the angle of curvature or bending radius of first accessory channel 110 and second accessory channel 112 is greater than the angle of curvature of distal end section 202 such that the distal portions of first accessory channel 110 and second accessory channel 112 extend outside the lumen of distal end section 202. To facilitate movement between the side-viewing and forward-viewing configurations, when viewed in cross-section, some ribs 114 may have a U- or V-shaped design with an open section that allows first accessory channel 110 and second accessory channel 112 to move freely in and out of ribs 114. Some proximal ribs 114 may have a circular outer circumference and may be circumferentially continuous, with no open section allowing first accessory channel 110 and second accessory channel 112 to move freely in and out of ribs 114.

To move pivot arm 206 from the forward-viewing configuration to the side-viewing configuration, first accessory channel 110 and second accessory channel 112 may be pushed in a distal direction relative to handle portion 104 and central portion 106, which applies a force through first accessory channel 110 and second accessory channel 112 to pivot arm 206. The resulting force causes pivot arm 206 to rotate about pivot point support member 208, thereby moving first accessory channel 110, second accessory channel 112, and pivot arm 206 into the side-viewing configuration. To move back to the forward-viewing configuration, a proximal force may be applied to first accessory channel 110 and second accessory channel 112 relative to handle portion 104 and central portion 106, thereby transferring the proximal force to pivot arm 206. The proximal force then causes pivot arm 206 to again rotate about pivot point support member 208 in the opposite direction, thereby moving first accessory channel 110, second accessory channel 112, and pivot arm 206 back to the forward-viewing configuration. To ensure that first accessory channel 110 and second accessory channel 112 move in unison during these movements, first accessory channel 110 and second accessory channel 112 may be secured together at any point along the length of endoscope system 100, or even along the entire length. In an example, first accessory channel 110 and second accessory channel 112 may be secured together using plastic tubing throughout the entire length of central portion 106. In another example, first accessory channel 110 and second accessory channel 112 may be secured together at the portions of first accessory channel 110 and second accessory channel 112 that extend outside the constraints of distal portion 102 when endoscope system 100 is in the side-viewing configuration. In further examples, a variety of other methods and structures may be used to assist in transitioning first accessory channel 110 and second accessory channel 112 between forward-viewing and side-viewing configurations. In other examples, rather than using single pivot arm 206, multiple pivot arms may be used, or a first pivot arm for first accessory channel 110 and a second pivot arm for second accessory channel 112. In still other examples, each of first accessory channel 110 and second accessory channel 112 may be moved between the forward-viewing and side-viewing configurations independently of each other. In still other examples, the degree of rotation of pivot arm 206 between the forward-viewing and side-viewing configuration may vary, potentially ranging from 45 degrees to greater than 135 degrees.

In addition to the ability to switch between forward-viewing and side-viewing configurations, distal portion 102 of endoscope system 100 may also bend and rotate as desired. FIG. 1 illustrates distal portion 102 in a straight configuration, while FIG. 2 illustrates distal portion 102 in a bent configuration. Endoscope system 100 may include a first drive member 116, a second drive member 118, and a third drive member 120. First drive member 116, second drive member 118, and third drive member 120 may extend through ribs 114. First drive member 116, second drive member 118, and third drive member 120 may be fixedly attached to distal end section 202 and extend through, or outside of the lumen to handle portion 104. First drive member 116 may be fixed on a wall of distal end section 202 while second drive member 118 and third drive member 120 may be fixed on opposing walls of distal end section 202. To move distal portion 102 from the straight configuration illustrated in FIG. 1 to the bent configuration illustrated in FIG. 2, first drive member 116 may be pulled in a proximal direction. The proximal movement of first drive member 116 may result in a force being applied through first drive member 116 and to distal end section 202. This force may cause the flexible, ribbed body of distal portion 102 to bend towards the configuration illustrated in FIG. 2. To move distal portion 102 back to a straight configuration, second drive member 118 and third drive member 120 may be pulled in a proximal direction. The proximal movement of second drive member 118 and third drive member 120 may result in a force being applied through second drive member 118 and third drive member 120 and to distal end section 202 that may move distal portion 102 back toward the straight configuration. In an example, distal portion 102 may include additional drive members fixedly attached to distal end section 202 and extend through or outside of the lumen to handle portion 104. First drive member 116, second drive member 118, and third drive member 120 may be drive mechanisms, deflection wires, or deflection cables.

First drive member 116, second drive member 118, and third drive member 120 may also secure individual ribs 114 of distal portion 102 together. First drive member 116, second drive member 118, and third drive member 120 may run through small holes in each individual rib 114, and sufficient tension may be applied to first drive member 116, second drive member 118, and third drive member 120 thereby securing ribs 114 together along first drive member 116, second drive member 118, and third drive member 120. Due to this design, ribs 114 may be shaped to allow for minimal contact between individual ribs 114. Each side of ribs 114 may be diamond-shaped when viewing endoscope system 100 from a side view as illustrated in FIGS. 1-3. The diamond shape reduces the contact points between each rib 114, thus minimizing friction and allowing for easier bending of distal portion 102 to the bent configuration and maximum flexibility. Optionally, first drive member 116, second drive member 118, and/or third drive member 120 may also include built-in electrical wiring that allows first drive member 116, second drive member 118, and/or third drive member 120 to function as a circuit for LED light 204 or plurality of LED lights 204. In other examples, ribs 114 may be connected together using a variety of other methods, such as with mechanical hinges, adhesives, and other well-known devices. Further, additional elongate members may extend through ribs 114 similar to first drive member 116, second drive member 118, and third drive member 120 to provide additional support to distal portion 102.

Alternatively, or additionally, in certain examples, an electrical wire 306 may be secured adjacent to a drive member such as first drive member 116 such that electrical wire 306 may function as a circuit for LED light 204 or plurality of LED lights 204 to provide power to LED light 204 or plurality of LED lights 204 from a power source. Electrical wire 306 may be secured adjacent to a drive member by an additional tube, mechanical features, or other means of integration allowing free movement of wiring during articulation of first drive member 116, second drive member 118, and third drive member 120 and/or first accessory channel 110 and second accessory channel 112. In other examples, an electrical wire 304 may be secured adjacent to features of ribs 114 such that electrical wire 304 may function as a circuit for LED light 204 or plurality of LED lights 204 to provide power to LED light 204 or plurality of LED lights 204 from a power source. Electrical wire 306 may be secured adjacent to ribs 114 via an additional tube, mechanical features, or other means of integration allowing free movement of wiring during articulation of first drive member 116, second drive member 118, and third drive member 120 to provide bending of distal portion 102 and/or first accessory channel 110 and second accessory channel 112. As illustrated in FIG. 3, an electrical wire 302 may be secured adjacent to first accessory channel 110. In still other examples, electrical wire 302 may be secured adjacent to second accessory channel 112. First accessory channel 110, second accessory channel 112, and electrical wire 302 may be secured together at the portions of first accessory channel 110 and second accessory channel 112 that extend outside the constraints of distal portion 102 when endoscope system 100 is in the side-viewing configuration. Alternatively, first accessory channel 110, second accessory channel 112, and electrical wire 302 may be secured together using plastic tubing throughout the entire length of central portion 106. Alternatively, electrical wire 302 may be integrated into first accessory channel 110 and/or second accessory channel 112 via reinforcement coil wiring, dedicated wire lumens, or other means of integration. Alternatively, electrical wire 302 may be secured adjacent to first accessory channel 110 and/or second accessory channel 112 via an additional tube, mechanical features, or other means of integration allowing free movement of wiring during articulation of first drive member 116, second drive member 118, and third drive member 120 and/or first accessory channel 110 and second accessory channel 112. Alternatively, electrical wire 302 may be included within a separate tube with the lumen of the distal portion, providing for free movement of the wiring during distal articulation. Electrical wire 302 may function as a circuit for LED light 204 or plurality of LED lights 204 to provide power to LED light 204 or plurality of LED lights 204 from a power source. In still other examples, fiber optic lighting cables may be integrated into first accessory channel 110 or second accessory channel 112 via one or more lumens dedicated to fiber optic lighting cables, overmolding, or other means of securing fiber optics within or along a wall of first accessory channel 110 or second accessory channel 112. Examples of a power source may include a battery. A power source may be included in pivot arm 206, distal portion 102, central portion 106, and/or handle portion 104. The power source may be alternating current ("AC"), a battery, or otherwise supplied, and may be internal or external to the body of the endoscope system or may be in any portion of a connected device. Electrical wires may pass from handle portion 104 to distal portion 102 between lights on a pivot arm and/or distal end section and a power source in handle portion 104.

Examples of connections between a distal end section and a pivot arm may include direct wiring between the distal end section and the pivot arm, the pivot point support member being a conductive element, the pivot point support member including an internal cavity configured to allow wire connectivity between device sections, and/or additional mechanical conductors or conductive features on the distal end section and/or the pivot arm configured to maintain connectivity between the distal end section and the pivot arm during articulation.

Figure 4:
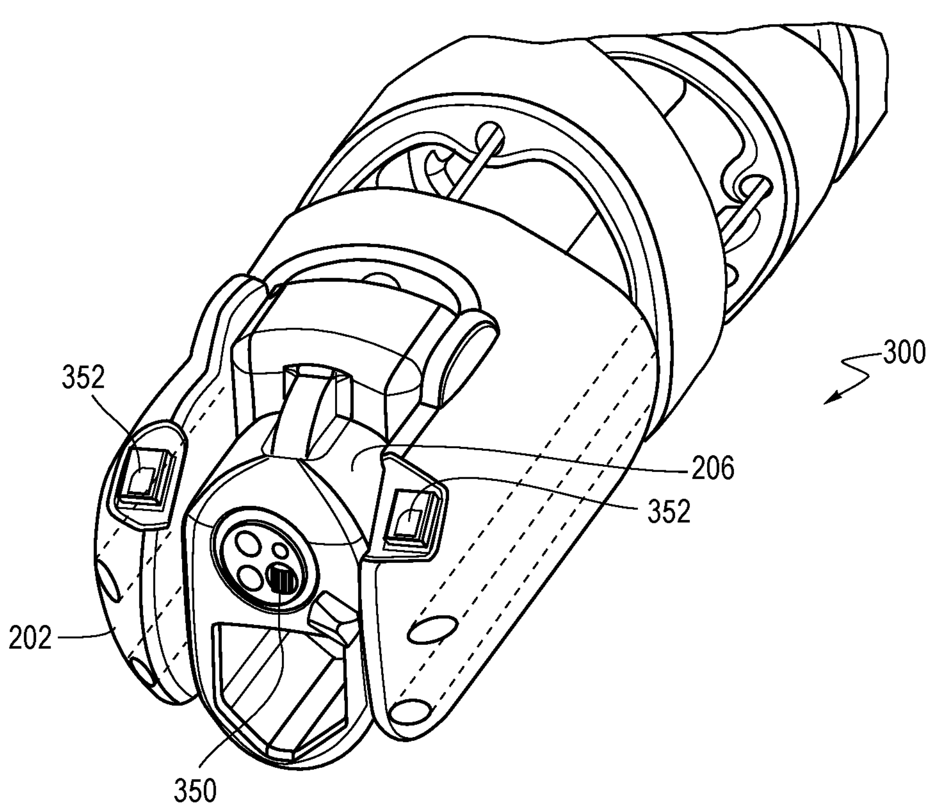
FIG. 4 illustrates a perspective view of yet another example of a distal portion of a steerable endoscopic system including lights on a distal end section, according to the principles of the present disclosure.

Referring to FIG. 4, a perspective view of yet another example of distal portion 300 of a steerable endoscopic system is illustrated, including lights 352 on a distal end section 202, and camera 350 in a catheter in pivot arm 206. Lights 352 are located only on distal end section 202 and not on pivot arm 206. Pivot arm 206 and/or distal portion 300 may be, or may include elements that are, fully transparent, partially transparent, or non-transparent.

Figure 5:
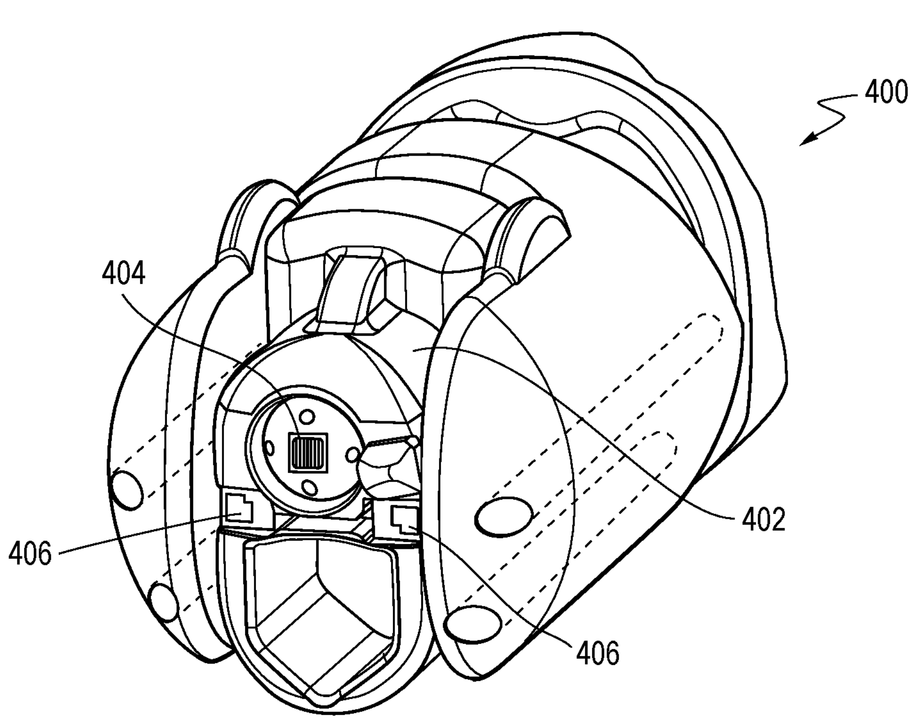
FIG. 5 illustrates a perspective view of yet another example of a distal portion of a steerable endoscopic system including lights on a pivot arm, according to the principles of the present disclosure.

Referring to FIG. 5, a perspective view of yet another example of distal portion 400 of a steerable endoscopic system is illustrated, including lights 406 on pivot arm 402, which also includes camera 404 in a catheter. Lights 406 are located only on pivot arm 402 and not on distal end section. Pivot arm 402 and/or distal portion 400 may be, or may include elements that are, fully transparent, partially transparent, or non-transparent. By placing lights 406 on pivot arm 402, alignment may be maintained at all times between camera 404 and illumination, throughout the full rotation of pivot arm 402 from forward-viewing configuration to side-viewing configuration. Examples of lights 406 may include light emitting diodes ("LEDs"), light fibers, light pipes, or any other components or methods for providing illumination. Lights may be integrated into any section of an endoscope system, including pivot arm 402, distal portion, rib(s), accessory channel(s), and/or central portion.

Figure 6:
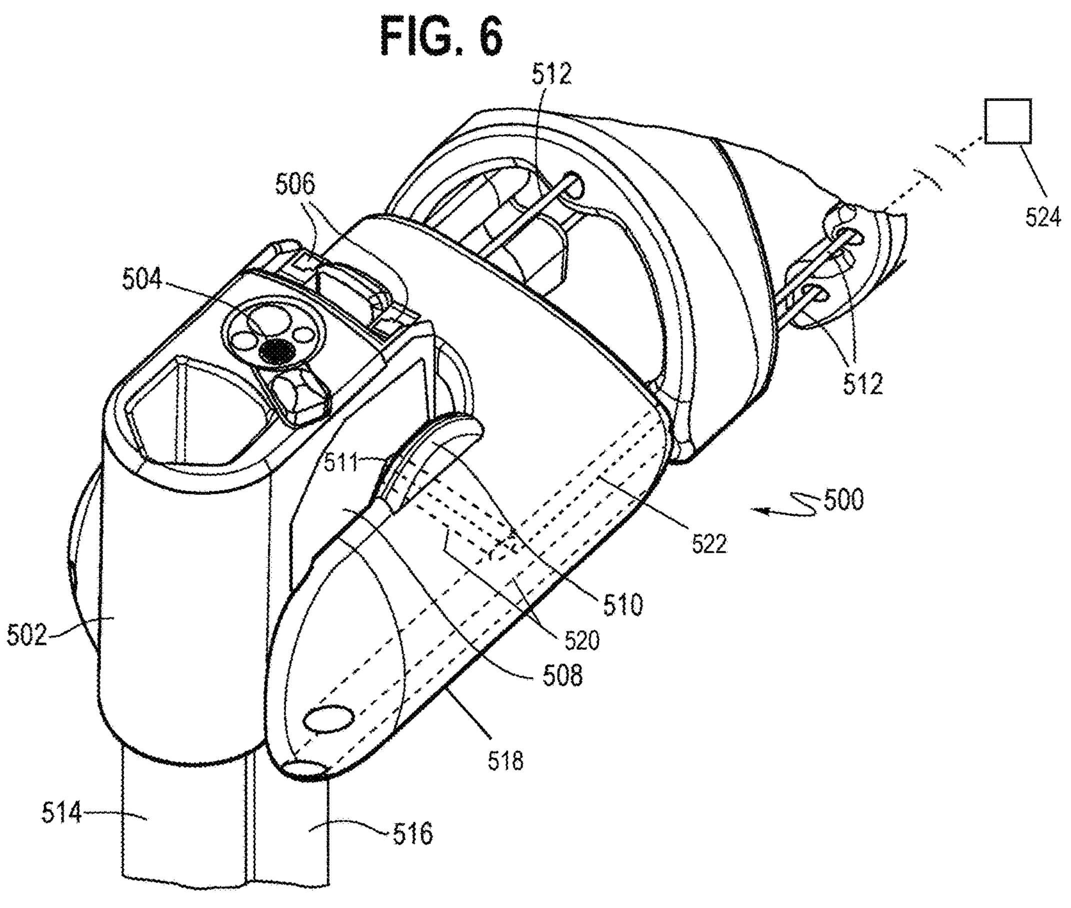
FIG. 6 illustrates a perspective view of yet another example of a distal portion of a steerable endoscopic system in a side-viewing configuration, including lights on a pivot arm, according to the principles of the present disclosure.

Referring to FIG. 6, a perspective view of yet another example of distal portion 500 of a steerable endoscope system is illustrated, in a side-viewing configuration, including lights 506 only on a pivot arm 502. As discussed hereinabove, pivot arm 502 may be moved into the side-viewing configuration by pushing first accessory channel 514 and second accessory channel 516 in a distal direction so that pivot arm 502 pivots about pivot point support member 510 defining a pivot point 511 and camera 504 and lights 506 are pointing towards a side view. Drive members 512 are visible fixedly attached to distal end section 518. Drive members 512 may be drive mechanisms, deflection wires, or deflection cables. On either side of pivot arm 502 is a conductive feature 508. Conductors 508 may connect to conductive features or conductors on and/or within distal end portion 518. Conductors 508 may be configured to maintain contact with conductive features or conductors on and/or within distal end portion 518 throughout the full rotation of pivot arm 502, ensuring connection between lights 506 and a power source 524. Pivot point support member 510 may include an internal cavity 520 configured to pass electrical wire 522 between pivot arm 502 and distal end section 518.

Figure 7:
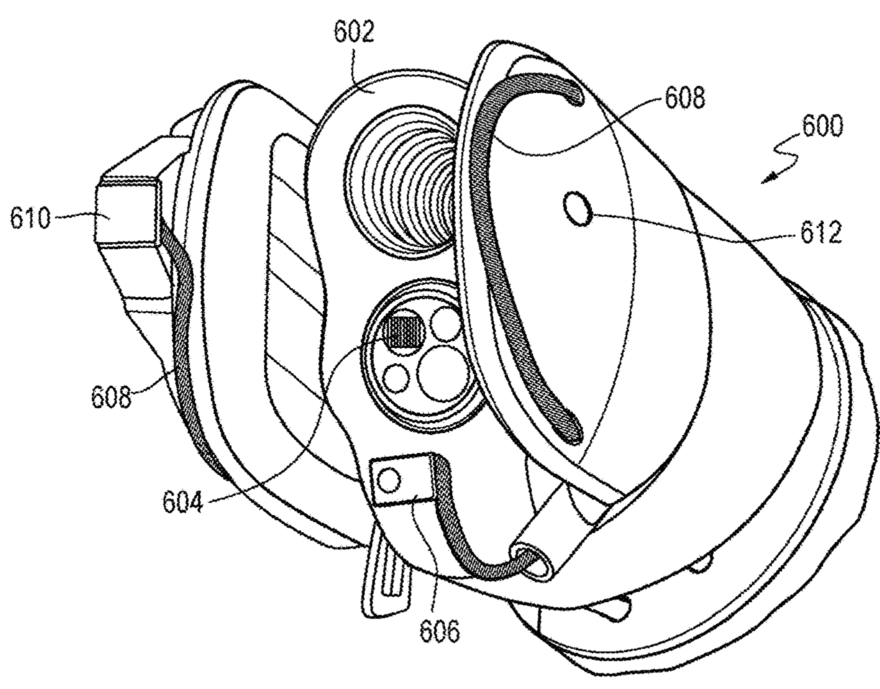
FIG. 7 illustrates a perspective view of yet another example of a distal portion of a steerable endoscopic system, including lights on a pivot arm and on a distal end section, according to the principles of the present disclosure.

Referring to FIG. 7, a perspective view of yet another example of distal portion 600 of a steerable endoscope system is illustrated, including light 606 on pivot arm 602 and light 610 on the distal end section. Pivot arm 602 is in a forward-viewing configuration in FIG. 7, with camera 604 facing forward, or facing distal to endoscope system. As illustrated in FIG. 7, electrical wire 608 includes pivot point support member 612 as a portion of the wiring conductive path from lights 606, 610 to the power source.

Figure 8:
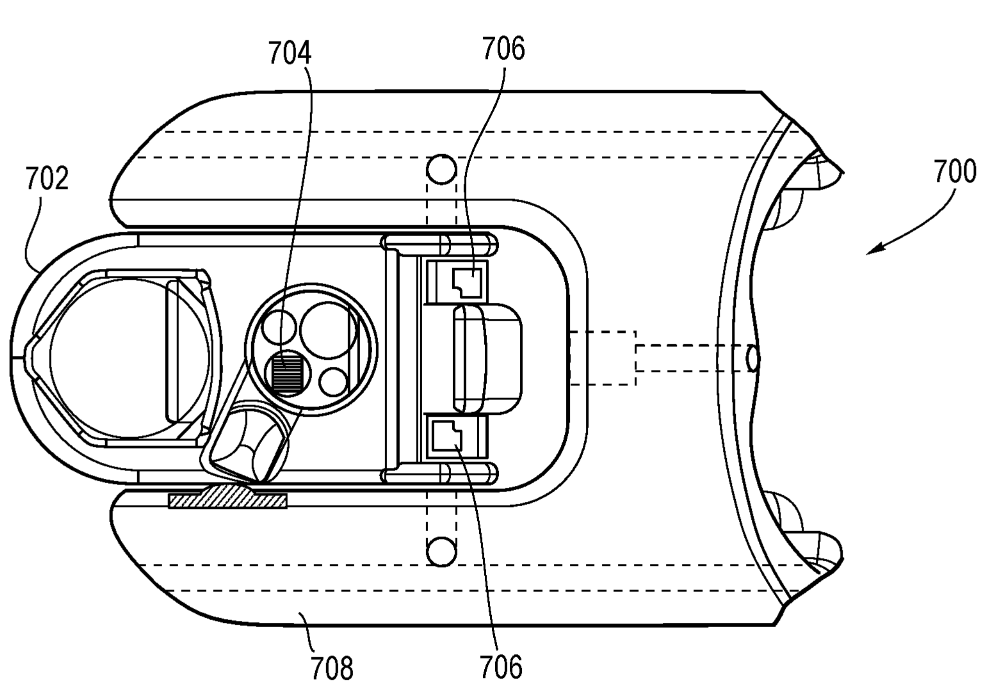
FIG. 8 illustrates a top view of yet another example of a distal portion of a steerable endoscopic system including a conductive feature on a distal end section.

Referring to FIG. 8, a top view of yet another example of a distal portion 700 of a steerable endoscopic system is illustrated, including a conductive feature 704 on a distal end section 708. Conductive feature 704 is configured to maintain connectivity between distal end section 708 and pivot arm 702 throughout the full rotation of pivot arm 702, ensuring connection between lights 706 and a power source.

Figure 9:
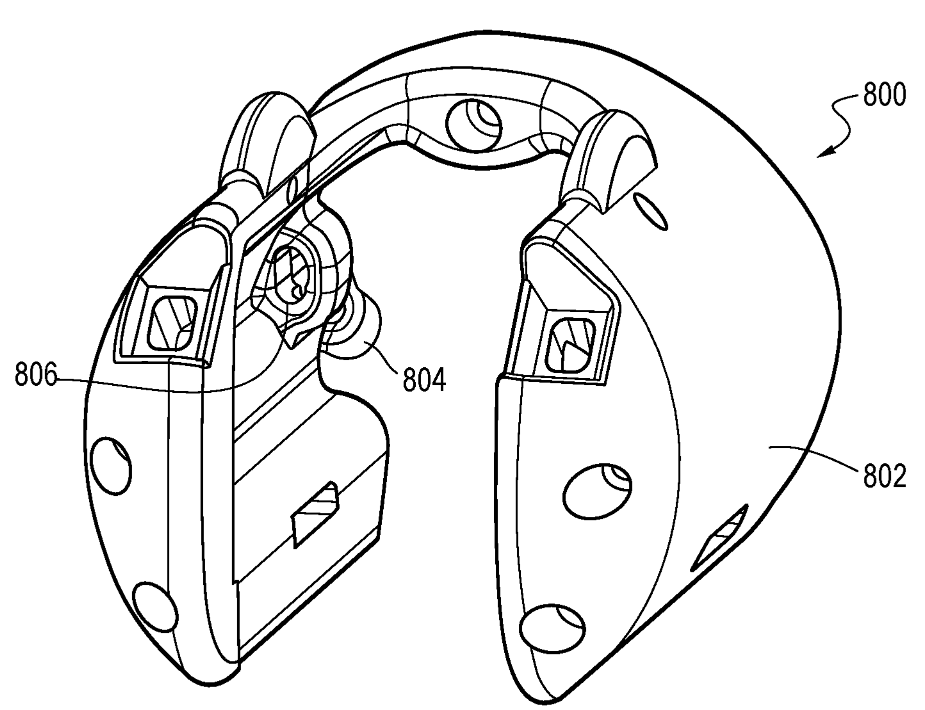
FIG. 9 illustrates a perspective view of an example of a distal end section of a steerable endoscopic system including a wire routing feature, according to the principles of the present disclosure.

Referring to FIG. 9, a perspective view of an example of a distal end section 800 of a steerable endoscopic system including wire routing features 802, 804 is illustrated. Wire routing features 802, 804 are configured to secure electrical wires adjacent to the distal portion rib features.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the disclosure may also relate, among others, to the following aspects:

A first aspect relates to a scope system, comprising: an elongate tube comprising a lumen extending therethrough, the elongate tube further comprising a distal portion comprising a distal end section, the distal end section comprising a pivot arm, the distal end section defining a forward direction parallel to a longitudinal direction parallel to a longitudinal direction of the distal end section; at least one accessory channel comprising a tubular structure, the tubular structure comprising an accessory lumen extending therethrough, the at least one accessory channel movably disposed at least partially within the lumen of the elongate tube, the at least one accessory channel comprising a distal section, the at least one accessory channel being movable between a forward-viewing configuration and a side-viewing configuration, a distal end of the at least one accessory channel attached to the pivot arm; and a plurality of lights located on and connected to the distal end section; wherein in the forward-viewing configuration, the distal section of the at least one accessory channel substantially faces in the forward direction; wherein in the side-viewing configuration, the distal section of the at least one accessory channel faces a direction that is angled relative to the forward direction; wherein during movement of the at least one accessory channel between the forward-viewing configuration and the side-viewing configuration, the at least one accessory channel and the pivot arm rotate about a pivot point, the pivot point being fixed relative to the distal end section of the elongate tube; and wherein one or more of the plurality of lights are distributed on and connected to the pivot arm.

A second aspect relates to the scope system of aspect 1, wherein the pivot arm is connected to the distal end section by a pivot point support member defining the pivot point; and wherein the pivot point support member comprises an electrical wire configured to connect the plurality of lights to a power source.

A third aspect relates to the scope system of any preceding aspect, wherein the pivot point support member comprises an internal cavity comprising the electrical wire configured to connect the one or more of the plurality of lights distributed on and connected to the pivot arm to a power source.

A fourth aspect relates to the scope system of any preceding aspect, wherein the pivot arm comprises at least one conductor configured to contact a second conductor of the distal end section throughout movement of the at least one accessory channel between the forward-viewing configuration and the side-viewing configuration.

A fifth aspect relates to the scope system of any preceding aspect, wherein the at least one accessory channel comprises a fiber optic lighting cable in a dedicated lumen in the at least one accessory channel, in overmolding on the at least one accessory channel, and/or within or along a wall of the at least one accessory channel.

A sixth aspect relates to the scope system of any preceding aspect, wherein the pivot arm and/or the distal end section are each independently fully transparent, partially transparent, or non-transparent.

A seventh aspect relates to the scope system of any preceding aspect, further comprising a power source connected to the plurality of lights.

An eighth aspect relates to the scope system of any preceding aspect, wherein the at least one accessory channel is configured to secure an electrical wire connecting the plurality of lights to a power source, and to permit free movement of the electrical wire during movement of the at least one accessory channel.

A ninth aspect relates to the scope system of any preceding aspect, wherein the distal portion comprises a plurality of individual ribs, at least one of the plurality of individual ribs comprising a substantially U-shaped cross-section comprising two sides and an opening; and wherein the plurality of individual ribs are configured to secure an electrical wire connecting the plurality of lights to a power source, and to permit free movement of the electrical wire during movement of the at least one accessory channel and/or bending of the distal portion.

A tenth aspect relates to the scope system of any preceding aspect, further comprising first and second deflection cables connected to the distal portion of the elongate tube and extending proximally along the elongate tube; wherein proximal movement of the first deflection cable bends the distal portion of the elongate tube in a first direction, and proximal movement of the second deflection cable bends the distal portion of the elongate tube in a second direction, the second direction opposite the first direction.

An eleventh aspect relates to the scope system of any preceding aspect, wherein the first deflection cable and/or the second deflection cable is configured to secure an electrical wire connecting the plurality of lights to a power source, and to permit free movement of the electrical wire during movement of the at least one accessory channel and/or bending of the distal portion.

A twelfth aspect relates to a scope system, comprising: an elongate tube comprising a lumen extending therethrough and a distal end section; and an accessory channel movably disposed at least partially within the lumen of the elongate tube; wherein a distal section of the accessory channel is rotatably moveable about a pivot point between a forward-facing direction and an angled direction, the pivot point being fixed relative to the distal end section of the elongate tube; and wherein a light is fixed to the distal section of the accessory channel such that when the distal section of the accessory channel rotates between the forward-facing direction and the angled direction, the light also rotates relative to the distal end section of the elongate tube.

In addition to the features mentioned in each of the independent aspects enumerated above, some examples may show, alone or in combination, the optional features mentioned in the dependent aspects and/or as disclosed in the description above and shown in the figures.

What is claimed is:

1. A scope system, comprising:

an elongate tube comprising a lumen extending therethrough, the elongate tube further comprising a distal portion comprising a distal end section, the distal end section comprising a pivot arm pivotably connected to the distal end section of the distal portion of the elongate tube by a pivot point support member at the distal end section of the elongate tube, the distal end section defining a forward direction parallel to a longitudinal direction of the distal end section;

at least one accessory channel comprising a tubular structure, the tubular structure comprising an accessory lumen extending therethrough, the at least one accessory channel movably disposed at least partially within the lumen of the elongate tube, the at least one accessory channel comprising a distal section, the at least one accessory channel being movable between a forward-viewing configuration and a side-viewing configuration, a distal end of the at least one accessory channel attached to the pivot arm; and a plurality of lights located on and connected to the distal end section;

wherein in the forward-viewing configuration, the distal section of the at least one accessory channel substantially faces in the forward direction;

wherein in the side-viewing configuration, the distal section of the at least one accessory channel faces a direction that is angled relative to the forward direction;

wherein during movement of the at least one accessory channel between the forward-viewing configuration and the side-viewing configuration, the at least one accessory channel and the pivot arm rotate about a pivot point, the pivot point being fixed relative to the distal end section of the elongate tube;

wherein one or more of the plurality of lights are distributed on and connected to the pivot arm; and wherein the pivot point support member comprises an internal cavity comprising an electrical wire configured to pass the electrical wire between the pivot arm and distal end section and to connect to the one or more of the plurality of lights distributed on and connected to the pivot arm to a power source.

2. The scope system of claim 1, wherein the at least one accessory channel comprises a fiber optic lighting cable in a dedicated lumen in the at least one accessory channel, in overmolding on the at least one accessory channel, and/or within or along a wall of the at least one accessory channel.

3. The scope system of claim 1, wherein the pivot arm and/or the distal end section are each independently fully transparent, partially transparent, or non-transparent.

4. The scope system of claim 1, further comprising a power source connected to the plurality of lights.

5. The scope system of claim 1, wherein the at least one accessory channel is configured to secure the electrical wire connecting the plurality of lights to the power source, and to permit free movement of the electrical wire during movement of the at least one accessory channel.

6. The scope system of claim 1, wherein the distal portion comprises a plurality of individual ribs, at least one of the plurality of individual ribs comprising a substantially U-shaped cross-section comprising two sides and an opening; and wherein the plurality of individual ribs are configured to secure the electrical wire connecting the plurality of lights to the power source, and to permit free movement of the electrical wire during movement of the at least one accessory channel and/or bending of the distal portion.

7. A scope system, comprising:

an elongate tube comprising a lumen extending therethrough, the elongate tube further comprising a distal portion comprising a distal end section, the distal end section comprising a pivot arm pivotably connected to the distal end section of the distal portion of the elongate tube by a pivot point support member at the distal end section of the elongate tube, the distal end section defining a forward direction parallel to a longitudinal direction of the distal end section;

at least one accessory channel comprising a tubular structure, the tubular structure comprising an accessory lumen extending therethrough, the at least one accessory channel movably disposed at least partially within the lumen of the elongate tube, the at least one accessory channel comprising a distal section, the at least one accessory channel being movable between a forward-viewing configuration and a side-viewing configuration, a distal end of the at least one accessory channel connected to the pivot arm;

a plurality of lights located on and connected to the distal end section; and first and second deflection cables connected to the distal portion of the elongate tube and extending proximally along the elongate tube;

wherein in the forward-viewing configuration, the distal section of the at least one accessory channel substantially faces in the forward direction;

wherein in the side-viewing configuration, the distal section of the at least one accessory channel faces a direction that is angled relative to the forward direction;

wherein the distal end section comprises a pivot arm, wherein during movement of the at least one accessory channel between the forward-viewing configuration and the side-viewing configuration, the at least one accessory channel and the pivot arm rotate about a pivot point, the pivot point being fixed relative to the distal end section of the elongate tube;

wherein one or more of the plurality of lights are distributed on and connected to the pivot arm;

wherein the pivot point support member comprises an internal cavity comprising an electrical wire configured to pass the electrical wire between the pivot arm and distal end section and to connect to the one or more of the plurality of lights distributed on and connected to the pivot arm to a power source; and wherein proximal movement of the first deflection cable bends the distal portion of the elongate tube in a first direction, and proximal movement of the second deflection cable bends the distal portion of the elongate tube in a second direction, the second direction opposite the first direction.

8. The scope system of claim 7, wherein the at least one accessory channel comprises a fiber optic lighting cable in a dedicated lumen in the at least one accessory channel, in overmolding on the at least one accessory channel, and/or within or along a wall of the at least one accessory channel.

9. The scope system of claim 7, wherein the pivot arm and/or the distal end section are each independently fully transparent, partially transparent, or non-transparent.

10. The scope system of claim 7, wherein the at least one accessory channel is configured to secure the electrical wire connecting the plurality of lights to the power source, and to permit free movement of the electrical wire during movement of the at least one accessory channel.

11. The scope system of claim 7, wherein the distal portion comprises a plurality of individual ribs, at least one of the plurality of individual ribs comprising a substantially U-shaped cross-section comprising two sides and an opening; and wherein the plurality of individual ribs are configured to secure the electrical wire connecting the plurality of lights to the power source, and to permit free movement of the electrical wire during movement of the at least one accessory channel and/or bending of the distal portion.

12. The scope system of claim 7, wherein the first deflection cable and/or the second deflection cable is configured to secure the electrical wire connecting the plurality of lights to the power source, and to permit free movement of the electrical wire during movement of the at least one accessory channel and/or bending of the distal portion.

13. A scope system, comprising:

an elongate tube comprising a lumen extending therethrough and a distal end section; and an accessory channel movably disposed at least partially within the lumen of the elongate tube;

wherein a distal section of the accessory channel is rotatably moveable about a pivot point between a forward-facing direction and an angled direction, the pivot point being fixed relative to the distal end section of the elongate tube;

wherein a light is fixed to the distal section of the accessory channel such that when the distal section of the accessory channel rotates between the forward-facing direction and the angled direction, the light also rotates relative to the distal end section of the elongate tube; and wherein the distal section of the accessory channel is connected to the distal end section by a pivot point support member on the distal end section of the elongate tube, wherein the pivot point support member defines the pivot point, wherein the pivot point support member comprises an internal cavity comprising an electrical wire configured to pass the electrical wire between the pivot arm and distal end section and to connect to the light on and connected to the distal end section to a power source.

* * * * *